United States Patent [19]

Matsuda et al.

[11] 4,231,967
[45] Nov. 4, 1980

[54] PROCESS FOR PRODUCING SALICYLALDEHYDE

[75] Inventors: Teruo Matsuda; Tetsuo Murata, both of Niihama, Japan

[73] Assignee: Sumitomo Chemical Company, Limited, Osaka, Japan

[21] Appl. No.: 46,933

[22] Filed: Jun. 8, 1979

[30] Foreign Application Priority Data

Jun. 13, 1978 [JP] Japan .................................. 53-71811

[51] Int. Cl.³ ............................................ C07C 45/00
[52] U.S. Cl. .................................................. 568/433
[58] Field of Search ..................................... 260/600 R

[56] References Cited

U.S. PATENT DOCUMENTS 4,151,201  4/1979  Casnati et al. ............... 260/600 R X Primary Examiner—Bernard Helfin
Attorney, Agent, or Firm—Cushman, Darby & Cushman

[57] ABSTRACT

Salicylaldehydes useful for perfumes, agricultural chemicals, chelating agents and the like are produced in high yield with high selectivity by reacting formaldehyde or its derivative with a corresponding phenol in a solvent using as a catalyst chromium or iron compounds.

5 Claims, No Drawings

PROCESS FOR PRODUCING SALICYLALDEHYDE

The present invention relates to a process for producing a salicylaldehyde of the formula (I),

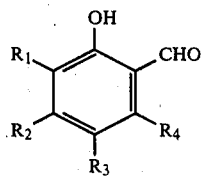

wherein $R_1$, $R_2$, $R_3$ and $R_4$ are each a hydrogen atom, an alkyl, cycloalkyl, alkoxyl or hydroxyl group or a halogen atom, by reaction between formaldehyde or its derivative and a phenol. The salicylaldehydes are important compounds in industry as intermediates for perfumes, agricultural chemicals or chelating agents, or as final products.

As is well known, the salicylaldehydes have so far been synthesized according to the so-called Reimer-Tiemann reaction. This process, however, has the following drawbacks: The yield of salicylaldehyde is low; and expensive chloroform is required in a large excess based on phenols and besides its recovery is almost impossible. These drawbacks can not be neglected from the standpoint of industrialization.

Consequently, the development of a process for producing salicylaldehydes at a low cost without using chloroform as starting material, has been demanded. One example of such process is disclosed in Japanese Patent Application Kokai (Laid-open) No. 34737/1978 wherein salicylaldehydes are produced in one step in the presence of a particular catalyst using phenols and formaldehydes as starting materials. This process may be considered as more favorable industrially than the Reimer-Tiemann process because it has few reaction steps and uses no expensive chloroform. But the yield by this process is not satisfactory. As a result of extensive study on this one-step process with a phenol and a formaldehyde as starting materials, the inventors found that high yields can be obtained by using chromium or iron compounds as catalyst.

The present invention provides a process for producing the salicylaldehyde of the formula (I), which comprises reacting a formaldehyde with a phenol of the formula (II),

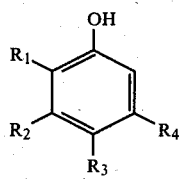

wherein $R_1$, $R_2$, $R_3$ and $R_4$ are as defined above, in a solvent using as a catalyst at least one member selected from the group consisting of chromium (III) acetylacetonate, organic or inorganic salts of chromium, iron acetylacetonate and organic salts of iron.

As the phenol represented by the formula (I), there may be given unsubstituted or substituted phenols. The substituted phenols include phenols having an alkyl group as substituent (e.g. o-cresol, m-cresol, p-cresol, 2-tert-butylphenol, 2-tert-butyl-4-methylphenol, 2,4-ditert-butylphenol, p-octylphenol); phenols having a cycloalkyl group as substituent (e.g. 2-cyclohexylphenol); phenols having an alkoxy group (e.g. 2-methoxyphenol, 4-methoxyphenol); phenols having a hydroxyl group (e.g. hydroquinone, catechol, resorcinol); and phenols having a halogen atom (e.g. 4-chlorophenol, 2-chlorophenol).

As the formaldehyde to be used in the present process, there may be given formaldehyde, para-formaldehyde, trioxan, methylal, dialkylformal, urotropin, 1,3-dioxolan and the like. Any of formaldehydes may be used so far as it substantially liberates formaldehyde under the present reaction conditions.

The catalyst used in the present invention includes chromium (III) acetylacetonate, organic or inorganic salts of chromium, iron acetylacetonate and organic salts of iron. Of these, particularly, chromium (III) acetylacetonate chromium formate, chromium acetate, chromium oxalate, chromium adipate, chromium benzoate, chromium bromide, chromium carbonate, chromium nitrate, iron acetylacetonate iron benzoate, iron salicylate and the like provide good results.

In order to further promote the catalytic action, an amine may be added to the reaction system. The amine includes pyridine, vinylpyridine, aliphatic tertiary amines, aromatic tertiary amines or quaternary amines.

As the solvent used in the present invention, hydrocarbons, ethers, esters and other solvents may be used. The hydrocarbons include pentane, hexane, benzene, cyclohexane, methylcyclohexane, toluene, ethylbenzene, cumene, decane, xylene, petroleum ether and the like. Ethers include furan, tetrahydrofuran, isopropyl ether and the like. Esters include methyl formate, methyl acetate, ethyl acetate, isopropyl acetate, butyl acetate, amyl acetate, cyclohexylacetate and the like. Other solvents include methylene chloride, carbon disulfide, chloroform, 1,1,1-trichloroethane, carbon tetrachloride, acetonitrile, dichloroethane, trichloroethylene, 1,2-dichloropropane, ethyl chloride, 1,2-dichloroethylene, 1,1,1,2-tetrachloroethane, 1,1,2,2-tetrachloroethane, pentachloroethane, hexachloroethane, acetic acid, formic acid, morpholine, chlorobenzene, dimethylformaldehyde, furfural, diethylformamide, dimethylsulfoxide, ethylene glycol diacetate, N-methylpyrrolidone, nitrobenzene, sulforane, glycerin, diethylene glycol dimethyl ether, diethylene glycol dibutyl ether and the like.

In the present invention, the reaction temperature is 150° to 210° C., inclusive of the both. A reaction temperature below 150° C. may be used, but it is not desirable because a long period of time is required for completion of the reaction. While, at a temperature above 210° C., the produced salicylaldehydes, objective compounds, cause side reactions. As a result, reaction results become poor. The reaction of the present invention proceeds most smoothly at a temperature of 160° to 190° C.

The molar ratio of the formaldehyde to the phenol is favorably 1 to 5.

The amount of catalyst depends upon the reaction temperature and reaction time, but generally the weight ratio of the catalyst to the phenol is preferably 0.5 to 0.0005.

The process of the present invention is carried out under atmospheric pressure to pressure slightly higher than that.

The present invention will be illustrated specifically with reference to the following examples, which are not however to be interpreted as limiting the invention thereto.

In the examples, all percentages are by mole unless otherwise stated. The conversion of phenols, yield of salicylaldehydes and selectivity of salicylaldehydes were obtained according to the following equations.

$$\text{Conversion of phenols (\%)} = \left(1 - \frac{\text{Residual amount of phenols (mole)}}{\text{Feed amount of phenols (mole)}}\right) \times 100$$

$$\text{Yield of salicylaldehydes (\%)} = \frac{\text{Amount of salicylaldehydes produced (mole)}}{\text{Feed amount of phenols (mole)}} \times 100$$

$$\text{Selectivity of salicylaldehydes (\%)} = \frac{\text{Yield of salicylaldehydes (\%)}}{\text{Conversion of phenols (\%)}} \times 100$$

EXAMPLES 1 TO 9

To a glass pressure reactor equipped with a thermometer and a stirrer were added 0.94 g (0.01 mole) of phenol, 0.9 g (0.03 mole) of paraformaldehyde and 20 ml of toluene, and then 0.2 g of a catalyst shown in Table 1 and 0.32 g (0.004 mole) of pyridine were added thereto. Reaction was carried out at 180° C. for 2 hours. Thereafter, the yield of salicylaldehyde was examined by gas chromatography. The results are shown in Table 1.

TABLE 1

| Example | Catalyst | Conversion of phenol (%) | Salicylaldehyde Yield (%) | Selectivity (%) |
|---|---|---|---|---|
| 1 | Chromium (III) acetylacetonate | 92.3 | 72.5 | 78.5 |
| 2 | Chromium formate | 89.2 | 74.4 | 83.4 |
| 3 | Chromium acetate | 91.0 | 71.8 | 78.9 |
| 4 | Chromium benzoate | 89.0 | 70.1 | 78.8 |
| 5 | Chromium bromide | 88.3 | 60.5 | 68.5 |
| 6 | Chromium carbonate | 87.8 | 62.8 | 71.5 |
| 7 | Chromium nitrate | 87.5 | 68.2 | 77.9 |
| 8 | Iron (III) acetylacetonate | 92.5 | 63.8 | 69.0 |
| 9 | Iron (III) salicylate | 89.9 | 67.5 | 75.1 |

EXAMPLE 10

Procedure was carried out in the same manner as in Example 1 except that 0.9 g (0.03 mole) of trioxane was used in place of paraformaldehyde. The yield of salicylaldehyde was 71.5%.

EXAMPLES 11 TO 13

Procedure was carried out in the same manner as in Example 1 except that the reaction temperature was varied as shown in Table 2. The results are shown in Table 2.

TABLE 2

| Example | Reaction temperature (°C.) | Conversion of phenol (%) | Salicylaldehyde Yield (%) | Selectivity (%) |
|---|---|---|---|---|
| 11 | 160 | 87.9 | 69.7 | 79.3 |
| 12 | 190 | 93.8 | 70.3 | 74.9 |
| 13 | 200 | 96.2 | 67.5 | 70.2 |

EXAMPLES 14 TO 16

Procedure was carried out in the same manner as in Example 3 except that the molar ratio of paraformaldehyde to phenol was varied as shown in Table 3. The results are shown in Table 3.

TABLE 3

| Example | Paraformaldehyde/phenol (molar ratio) | Conversion of phenol (%) | Salicylaldehyde Yield (%) | Selectivity (%) |
|---|---|---|---|---|
| 14 | 1.5 | 72.5 | 65.8 | 90.8 |
| 15 | 2.5 | 89.6 | 71.5 | 79.8 |
| 16 | 4.0 | 95.2 | 69.4 | 72.9 |

EXAMPLES 17 TO 21

Procedure was carried out in the same manner as in Example 1 except that the amount of chromium (III) acetylacetonate and reaction time were varied as shown in Table 4. The results are shown in Table 4.

TABLE 4

| Example | Amount of catalyst (g) | Reaction time (hr) | Conversion of phenol (%) | Salicylaldehyde Yield (%) | Selectivity (%) |
|---|---|---|---|---|---|
| 17 | 0.02 | 2 | 92.3 | 74.7 | 80.9 |
| 18 | 0.01 | 2 | 94.5 | 75.4 | 79.8 |
| 19 | 0.005 | 2 | 90.5 | 68.3 | 75.5 |
| 20 | 0.002 | 2 | 89.0 | 66.3 | 74.5 |
| 21 | 0.002 | 4 | 95.8 | 69.0 | 72.0 |

EXAMPLES 22 TO 26

Procedure was carried out in the same manner as in Example 1 except that pyridine was replaced by amines shown in Table 5 and that the reaction time was changed to 4 hours. The results are shown in Table 5.

TABLE 5

| Example | Amines | Conversion of phenol (%) | Salicylaldehyde Yield (%) | Selectivity (%) |
|---|---|---|---|---|
| 22 | Not used | 81.0 | 63.0 | 77.8 |
| 23 | Triethylamine | 85.2 | 61.2 | 71.8 |
| 24 | α,α'-Dipyridine | 83.5 | 66.5 | 79.6 |
| 25 | β-Picoline | 89.8 | 68.7 | 76.5 |
| 26 | Vinylpyridine | 84.5 | 62.2 | 73.6 |

EXAMPLES 27 TO 31

Procedure was carried out in the same manner as in Example 1 except that toluene was replaced by solvents shown in Table 6. The results are shown in Table 6.

TABLE 6

| Example | Solvent | Conversion of phenol (%) | Salicylaldehyde Yield (%) | Selectivity (%) |
|---|---|---|---|---|
| 27 | Xylene | 89.3 | 69.8 | 78.2 |
| 28 | Ditolylethane | 87.4 | 68.3 | 78.1 |
| 29 | Chlorobenzene | 91.0 | 71.3 | 78.4 |
| 30 | Phenyl ether | 89.9 | 70.1 | 79.1 |
| 31 | n-Butyl acetate | 86.7 | 67.4 | 77.7 |

EXAMPLES 32 TO 35

Procedure was carried out in the same manner as in Example 1 except that phenol was replaced by phenols shown in Table 7. The results are shown in Table 7.

TABLE 7

| Example | Phenols | Product | Yield of salicylaldehydes (%) |
|---|---|---|---|
| 32 | HO–⬡–Cl | OHC–⬡(HO)–Cl | 61.1 |
| 33 | HO–⬡–OCH₃ | OHC–⬡(HO)–OCH₃ | 78.3 |
| 34 | HO–⬡–CH₃ | OHC–⬡(HO)–CH₃ | 88.1 |
| 35 | HO–⬡–C₈H₁₇ | OHC–⬡(HO)–C₈H₁₇ | 82.4 |

What is claimed is:

1. A process for producing a salicylaldehyde of the formula (I),

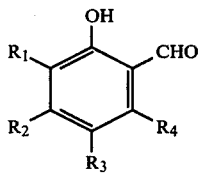 (I)

wherein $R_1$, $R_2$, $R_3$ and $R_4$ are each a hydrogen atom, an alkyl, cycloalkyl, alkoxyl or hydroxyl group or a halogen atom, which comprises reacting formaldehyde or a formaldehyde liberating compound with a phenol of the formula (II),

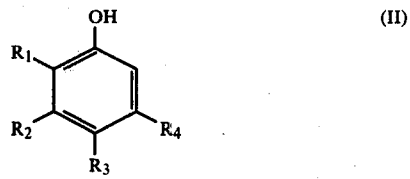 (II)

wherein $R_1$, $R_2$, $R_3$ and $R_4$ are as defined above, in a solvent using as a catalyst at least one member selected from the group consisting of chromium (III) acetylacetonate, chromium formate, chromium acetate, chromium oxalate, chromium adipate, chromium benzoate, chromium bromide, chromium carbonate, chromium nitrate, iron acetylacetonate, iron benzoate and iron salicylate, at a temperature of 150° to 210° C.

2. A process according to claim 1 wherein the phenol is phenol per se o-,m- or p-cresol, 2-tert.-butylphenol, 2-tert.-butyl-4-methoxyphenol, 2,4-di-tert.-butylphenol, p-octylphenol, 2-cyclohexylphenol, 2- or 4-methoxyphenol, hydroquinone, catechol, resorcinol or 2-or 4-chlorophenol.

3. A process according to claim 2 wherein the phenol is phenol per se and the product obtained is salicylaldehyde.

4. A process according to claim 1, wherein the molar ratio of the formaldehyde on formaldehyde liberating compound to the phenol is 1 to 5.

5. A process according to claim 1, wherein the weight ratio of the catalyst to the phenol is 0.0005 to 0.5.